US00PP25639P2

(12) United States Plant Patent
Kievit

(10) Patent No.: US PP25,639 P2
(45) Date of Patent: Jun. 23, 2015

(54) ***PEROVSKIA* PLANT NAMED 'CRAZYBLUE'**

(50) Latin Name: *Perovskia atriplicifolia*
Varietal Denomination: CrazyBlue

(71) Applicant: Ball Horticultural Company, West Chicago, IL (US)

(72) Inventor: Christa Kievit, Hem (NL)

(73) Assignee: Ball Horticultural Company, West Chicago, IL (US)

( * ) Notice: Subject to any disclaimer, the term of this patent is extended or adjusted under 35 U.S.C. 154(b) by 137 days.

(21) Appl. No.: 13/987,976

(22) Filed: Sep. 20, 2013

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — Anne Grunberg
(74) *Attorney, Agent, or Firm* — Audrey Charles

(57) ABSTRACT

A new and distinct cultivar of *Perovskia* plant named 'CrazyBlue', characterized by its violet-blue colored flowers, greyed-green colored foliage, and moderately vigorous, compact-mounded growth habit, is disclosed.

2 Drawing Sheets

Latin name of genus and species of plant claimed: *Perovskia atriplicifolia.*
Variety denomination: 'CrazyBlue'.

BACKGROUND OF THE INVENTION

The present invention relates to a new and distinct cultivar of *Perovskia* plant botanically known as *Perovskia atriplicifolia* and hereinafter referred to by the cultivar name 'CrazyBlue'.

The new cultivar originated in a controlled breeding program in Hem, The Netherlands during September 2009. The objective of the breeding program was the development of compact, well branched *Perovskia.*

The new *Perovskia* cultivar is the result of open-pollination within an insect-caged environment. The female (seed) parent of the new cultivar is a *Perovskia atriplicifolia* species selection, not patented and not coded, characterized by its violet-blue colored flowers, greyed-green colored foliage, and moderately vigorous, compact-mounded growth habit. The male (pollen) parent of the new cultivar is from a group of *Perovskia atriplicifolia* species plants, not patented and not coded, selected primarily for their well-branched growth habits and further characterized by violet-blue colored flowers, greyed-green colored foliage, and moderately vigorous, mounded growth habits. The new cultivar was discovered and selected as a single flowering plant within the progeny of the above stated open-pollination during August 2010 in a controlled environment in Hem, The Netherlands.

Asexual reproduction of the new cultivar by terminal stem cuttings since August 2010 in Elburn, Ill. and Hem, The Netherlands has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'CrazyBlue' as a new and distinct cultivar of *Perovskia* plant:

1. Violet-blue colored flowers;
2. Greyed-green colored foliage; and
3. Moderately vigorous, compact-mounded growth habit.

Plants of the new cultivar differ from plants of the female and possible male parents primarily in have a better branched and more compact growth habit.

Of the many commercially available *Perovskia* cultivars, the most similar in comparison to the new cultivar is Lacey Blue 'Lisslitt' U.S. Plant Pat. No. 20,845. However, in side by side comparisons, plants of the new cultivar differ from plants of 'Lisslitt' in at least the following characteristics:

1. Plants of the new cultivar are shorter than plants of 'Lisslitt'; and
2. Plants of the new cultivar have a darker colored calyx than plants of 'Lisslitt'.

In addition, plants of the new cultivar can be compared to plants of 'Little Spire' U.S. Plant Pat. No. 11,643. In side by side comparisons, plants of the new cultivar differ from plants of 'Little Spire' in at least the following characteristics:

3. Plants of the new cultivar are shorter than plants of 'Little Spire'; and
4. Plants of the new cultivar have larger flowers than plants of 'Little Spire'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'CrazyBlue'. The plants were grown in one-gallon containers for 14 weeks in a greenhouse in West Chicago, Ill. Plants were given two pinches, one prior to and one at transplant.

DETAILED BOTANICAL DESCRIPTION

Figure 1:
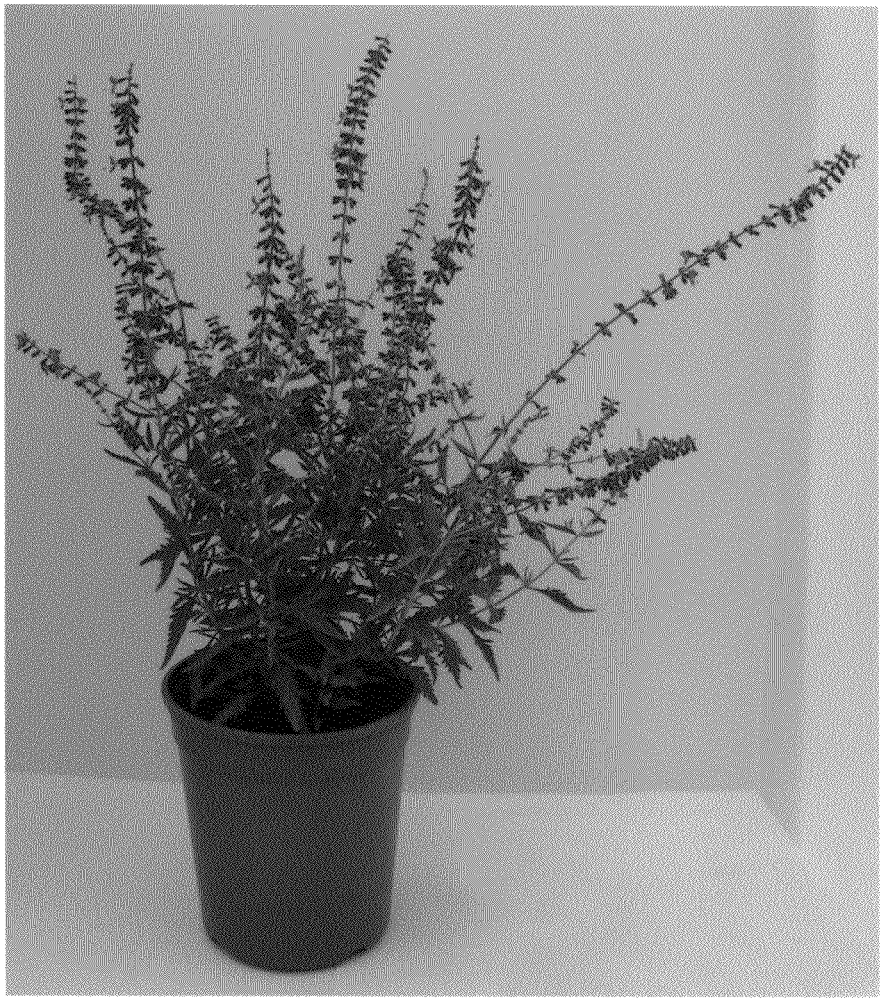
FIG. 1 illustrates a side view of the overall growth and flowering habit of 'CrazyBlue'.
Figure 2:
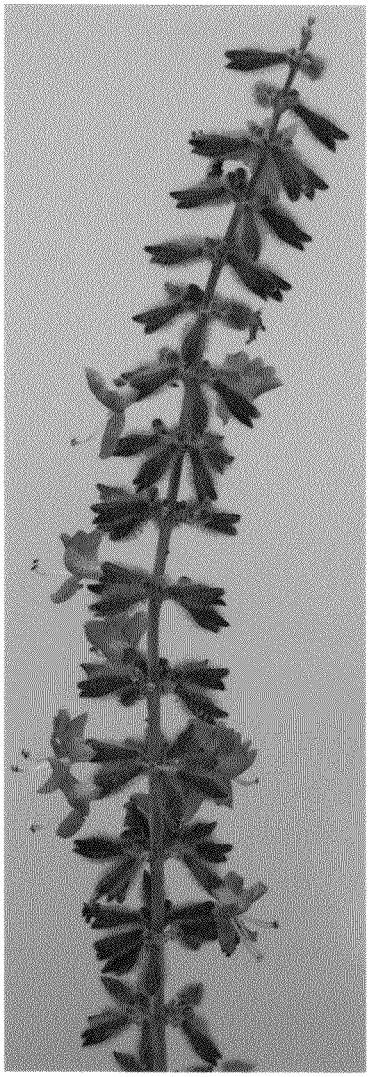
FIG. 2 illustrates a close-up view of an individual inflorescence of 'CrazyBlue'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in August 2013 under natural light conditions in West Chicago, Ill.

The following descriptions and measurements describe plants produced from cuttings from stock plants and grown in a glass-covered greenhouse under conditions comparable to those used in commercial practice. The plants were grown in Elburn, Ill. in one-gallon containers for 14 weeks utilizing a soilless growth medium. Plants were given two pinches, one prior to and one at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Perovskia atriplicifolia* cultivar CrazyBlue.

Parentage:

*Female parent.*—A *Perovskia atriplicifolia* species selection, not patented and not coded.

*Male parent.*—A group of *Perovskia atriplicifolia* species plants, not patented and not coded.

Propagation:

*Type cutting.*—Terminal stem.

*Time to initiate roots.*—Approximately 10 to 12 days.

*Time to produce a rooted cutting.*—Approximately 5 to 6 weeks.

*Root description.*—Fine, fibrous white to brown in color.

*Rooting habit.*—Freely branching.

Plant description:

*Commercial crop time.*—Approximately 12 to 14 weeks from a rooted cutting to finish in a one-gallon container.

*Growth habit and general appearance.*—Moderately vigorous, compact-mounded.

*Size.*—Height from soil level to top of plant plane: Approximately 42.0 cm. Width: Approximately 49.0 cm.

*Branching habit.*—Freely branching. Pinching enhances lateral branching. Quantity of branches per plant: Approximately 9.

*Branch.*—Shape: Square in cross section becoming round with age. Strength: Strong. Length to base of inflorescence: Approximately 15.0 cm. Diameter: Approximately 3.0 mm. Length of central internode: Approximately 1.2 cm. Texture: Densely pubescent with a mixture of stellate and single hairs. Color of young stems: 190A to 190B. Color of mature stems: 190B to 190C with woody base of 200B.

Foliage description:

*General description.*—Quantity of leaves per branch: Approximately 12. Fragrance: Strong, sage-like. Form: Simple. Arrangement: Opposite.

*Leaves.*—Aspect: Primarily perpendicular to stem. Shape: Ovate. Margin: Incised. Apex: Acute. Base: Cuneate. Venation pattern: Pinnate. Length of mature leaf: Approximately 7.5 cm. Width of mature leaf: Approximately 2.0 cm. Texture of upper and lower surfaces: Moderately pubescent with stellate hairs and glands. Color of upper surface of young foliage: Closest to but darker than 191A with venation of 191C. Color of lower surface of young foliage: 191A with venation of 191C. Color of upper surface of mature foliage: N137D with midvein of 191C. Color of lower surface of mature foliage: 137B with midvein of 147C.

*Petiole.*—Length: Approximately 4.0 mm. Diameter: Approximately 1.0 mm. Texture: Densely pubescent with stellate hairs. Color: 147C.

Flowering description:

*Flowering habit.*—'CrazyBlue' is freely flowering under outdoor growing conditions blooming from late spring through summer.

*Lastingness of individual flower.*—Approximately 5 to 7 days.

Inflorescence description:

*General description.*—Type: Terminal panicles of verticillasters, each panicle having about 6 branches. Flowers not persistent, facing outward and downward. Quantity of inflorescences per plant: Approximately 9. Fragrance: Not detected. Depth or height of inflorescence: Approximately 27.0 cm. Width: Approximately 2.0 cm. Quantity of flowers per inflorescence: Approximately 90, opening from base to apex.

*Rachis.*—Shape: Square in cross section. Strength: Strong. Length: Approximately 27.0 cm. Diameter: Approximately 2.0 to 3.0 mm. Texture: Densely pubescent with a mixture of stellate and single hairs. Color: 190A to 190B.

Flower description:

*Type.*—Single, bilabiate, approximately 6 per verticillaster.

*Bud.*—Rate of opening: Generally takes 2 to 3 days for bud to progress from first color to fully open flower.

*Bud just before opening.*—Shape: Obovoid. Length: Approximately 5.0 mm. Diameter: Approximately 2.0 mm. Texture: Densely pubescent. Color: N92D with pubescence of 91B.

*Corolla.*—Shape: 5 lobes arranged in two lips fused into a tube at base, upper lip of 4 lobes. Depth: Approximately 1.1 cm. Width: Approximately 6.0 mm. Length: Approximately 9.0 mm.

*Upper lip.*—Shape: 4-lobed. Margin: Entire, curl slightly backwards. Apex: Rounded. Length from throat: Approximately 3.0 mm. Width: Approximately 6.0 mm. Texture of inner surface: Glabrous. Texture of outer surface: Sparsely pubescent. Color of inner surface when first and fully open: 94A. Color of outer surface when first and fully open: 94B.

*Lower lip.*—Shape: Oblong. Margin: Entire, somewhat wavy. Apex: Rounded. Length from throat: Approximately 5.0 mm. Width: Approximately 3.0 mm. Texture of inner surface: Glabrous. Texture of outer surface: Sparsely pubescent. Color of inner surface when first and fully open: 94A. Color of outer surface when first and fully open: 94B.

*Corolla tube.*—Length: Approximately 7.0 mm. Width: Approximately 2.0 mm. Texture of inner surface: Densely pubescent at throat opening. Texture of outer surface: Moderately pubescent. Color: NN155D at base transitioning to 94D at throat.

*Calyx.*—Shape: Tubular, persistent for a few weeks after petals drop. Length: Approximately 5.0 mm. Diameter: Approximately 2.0 mm.

*Sepals.*—Quantity per flower: 5, fused at base. Apex: Acute to rounded. Margin of free portion: Entire. Length: Approximately 5.0 mm. Width: Less than 1.0 mm. Texture of inner surface: Glabrous. Texture of outer surface: Densely pubescent with long hairs and glands. Color of inner surface: N137B. Color of outer surface: N137A with a heavy overlay of N92D and pubescence of 91B.

*Pedicels.*—Strength: Strong, flexible. Length: Approximately 1.0 mm. Diameter: Less than 1.0 mm. Texture: Densely pubescent. Color: N137A with a heavy overlay of N92D and pubescence of NN155D.

*Reproductive organs.*—Androecium: Stamen quantity: 4 per flower, 2 vestigial, adnate to corolla and exserted. Filament length: Approximately 1.2 cm. Filament length of fixed portion: Approximately 6.0 mm. Filament color: NN155D, opaque and tinted with 94A near anther. Anther shape: Oval, 2-celled. Anther length: Approximately 1.0 mm. Anther color: 94C. Pollen amount: None observed. Gynoecium: Pistil quantity: 1 per flower. Pistil length: Approximately 7.0 mm. Stigma shape: Bifid. Stigma width: Approximately 1.0 mm. Stigma color: NN155D, opaque and tinted with 145D. Style length: Approximately 6.0 mm. Style color: NN155D, opaque and tinted with 94A near stigma. Ovary length: Approximately 1.0 mm. Ovary color: N144D.

Seed and fruit production: Neither seed nor fruit production has been observed.

Disease and pest resistance: Resistance to pathogens and pests common to *Perovskia* has not been observed.

What is claimed is:

1. A new and distinct cultivar of *Perovskia* plant named 'CrazyBlue', substantially as herein illustrated and described.

* * * * *